(12) United States Patent
Pilant

(10) Patent No.: US 11,160,745 B2
(45) Date of Patent: Nov. 2, 2021

(54) METHODS AND COMPOSITIONS FOR TOPICAL DELIVERY FOR SKIN CARE

(71) Applicant: Gregory P. Pilant, Gordonsville, TN (US)

(72) Inventor: Gregory P. Pilant, Gordonsville, TN (US)

(*) Notice: Subject to any disclaimer, the term of this patent is extended or adjusted under 35 U.S.C. 154(b) by 0 days.

(21) Appl. No.: 15/312,578

(22) PCT Filed: Apr. 17, 2015

(86) PCT No.: PCT/US2015/026342
§ 371 (c)(1),
(2) Date: Nov. 18, 2016

(87) PCT Pub. No.: WO2015/161179
PCT Pub. Date: Oct. 22, 2015

(65) Prior Publication Data
US 2017/0202769 A1    Jul. 20, 2017

Related U.S. Application Data

(60) Provisional application No. 61/981,287, filed on Apr. 18, 2014.

(51) Int. Cl.
| | | |
|---|---|---|
| *A61K 8/27* | (2006.01) | |
| *A61K 8/19* | (2006.01) | |
| *A61K 8/97* | (2017.01) | |
| *A61K 8/67* | (2006.01) | |
| *A61Q 19/00* | (2006.01) | |
| *A61K 8/65* | (2006.01) | |
| *A61Q 19/08* | (2006.01) | |
| *A61K 33/06* | (2006.01) | |
| *A61K 8/64* | (2006.01) | |
| *A61K 33/00* | (2006.01) | |
| *A61Q 19/02* | (2006.01) | |
| *A61K 38/08* | (2019.01) | |
| *A61K 36/52* | (2006.01) | |
| *A61K 33/30* | (2006.01) | |
| *A61K 36/48* | (2006.01) | |
| *A61K 36/49* | (2006.01) | |
| *A61Q 19/06* | (2006.01) | |
| *A61K 38/17* | (2006.01) | |

(52) U.S. Cl.
CPC .................. *A61K 8/65* (2013.01); *A61K 8/19* (2013.01); *A61K 8/27* (2013.01); *A61K 8/64* (2013.01); *A61K 33/00* (2013.01); *A61K 33/06* (2013.01); *A61K 33/30* (2013.01); *A61K 36/48* (2013.01); *A61K 36/49* (2013.01); *A61K 36/52* (2013.01); *A61K 38/08* (2013.01); *A61K 38/177* (2013.01); *A61Q 19/00* (2013.01); *A61Q 19/008* (2013.01); *A61Q 19/02* (2013.01); *A61Q 19/06* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 4,743,442 A * | 5/1988 | Raaf ...................... | A61K 8/671 424/47 |
| 6,620,419 B1 | 9/2003 | Lintner | |
| 7,569,558 B2 | 8/2009 | Gupta | |
| 7,855,179 B2 | 12/2010 | Vrijbloed et al. | |
| 8,575,106 B2 | 11/2013 | Santhanam et al. | |
| 8,617,580 B2 | 12/2013 | Toledano et al. | |
| 8,674,072 B2 | 3/2014 | Dal Farra et al. | |
| 2004/0037910 A1* | 2/2004 | Hon ....................... | A61K 33/00 424/771 |
| 2004/0127420 A1 | 7/2004 | Quirk | |
| 2005/0118124 A1* | 6/2005 | Reinhart ................... | A61K 8/64 424/63 |
| 2005/0118279 A1 | 6/2005 | Blotsky et al. | |
| 2006/0183708 A1 | 8/2006 | Gupta | |
| 2007/0148118 A1 | 6/2007 | Montanari et al. | |
| 2008/0107679 A1* | 5/2008 | Dilallo ..................... | A61K 8/64 424/195.17 |
| 2010/0055138 A1* | 3/2010 | Margulies ................. | A61K 8/02 424/401 |
| 2010/0145255 A1* | 6/2010 | Popescu ................... | A61K 8/43 604/20 |

(Continued)

FOREIGN PATENT DOCUMENTS

| | | |
|---|---|---|
| EP | 0934773 B1 | 2/2004 |
| EP | 1959975 B1 | 3/2013 |

OTHER PUBLICATIONS

Acetyl hexapeptide-3, ChemIDPlus, accessed Aug. 30, 2018 at URL chem.nlm.nih.gov/chemidplus/sid/0616204229, pp. 1-3. (Year: 2018).*
Ruiz et al., "Preparation and stability of cosmetic formulations with and antiaging peptide," J. Cosmet. Sci. 58:157-171 (2007) (Year: 2007).*
Argireline, PubChem CID 11228338, accessed at 2018 at pubchem.ncbi.nlm.nih.gov/compound/Argireline, pp. 1-20. (Year: 2018).*
Valyltryptophan, PubChem CID 3360287, accessed Aug. 3, 2020 at pubchem.ncbi.nlm.nih.gov/compound/3360287, pp. 1-34 (Year: 2020).*
Tetrapeptide-3 (PubChem CID 71417597, accessed Aug. 3, 2020 at pubchem.ncbi.nlm.nih.gov/compound/71417597, pp. 1-22 (Year: 2020).*

(Continued)

*Primary Examiner* — Julie Ha
*Assistant Examiner* — Kristina M Hellman
(74) *Attorney, Agent, or Firm* — Singleton Law, PLLC; Chainey P. Singleton

(57) ABSTRACT

The present invention provides a topical composition for application to a keratinous tissue comprising a cosmetically or pharmaceutically acceptable carrier; one or more selected from potassium, zinc, calcium, rubidium disposed in the cosmetically or pharmaceutically acceptable carrier; and one or more peptides disposed in the cosmetically or pharmaceutically acceptable carrier.

13 Claims, No Drawings

(56) References Cited

U.S. PATENT DOCUMENTS

2010/0239695 A1  9/2010  Vielhaber et al.

OTHER PUBLICATIONS

Namjoshi et al., "Skin peptides: biological activity and therapeutic opportunities," Journal of pharmaceutical sciences 97: 2524-2542 (2008) (Year: 2008).*
International Search Report of Korean Intellectual Property Office for PCT/US2015/026342 dated Jun. 29, 2015, 19 pp.

* cited by examiner

METHODS AND COMPOSITIONS FOR TOPICAL DELIVERY FOR SKIN CARE

CROSS REFERENCE TO RELATED APPLICATIONS

This application claims priority to, and is the National Phase of International Application No. PCT/US2015/026342, filed on Apr. 17, 2015, which claims the benefit under 35 U.S.C. § 119(e) of U.S. Provisional Application No. 61/981,287 filed Apr. 18, 2014, the content of each of which is incorporated by reference herein.

TECHNICAL FIELD OF THE INVENTION

The present invention relates generally to methods and compositions for topical application which comprise metal peptide complexes provide specific benefits to the skin.

BACKGROUND OF THE INVENTION

Without limiting the scope of the invention, its background is described in connection with topical application. Generally, consumers seek to improve the appearance of their skin and hair including the visible signs of aging, discoloration, hyper-pigmentation, redness, inflammation, and over-production of oils and/or lipids at the skin surface. In addition, collagen synthesis and degradation also play a role in common skin concerns. Collagen is the body's major structural protein and gives skin strength, durability, and a smooth, plump appearance. It is created by fibroblasts, specialized skin cells located in the dermis, in a process that involves conversion of preprocollagen I to procollagen I and eventually to tropocollagen, the form that forms collagen fibers. For example, a reduction in collagen I is associated with loss of firmness and elasticity of skin and leads to wrinkling associated with aging. Hyaluronic acid is another component of skin that plays a role in its aesthetic appearance including, for example, changes in tissue hydration, as well as plumpness and protection against free radicals. With age, however, glycosaminoglycan (GAG) synthesis and overall GAG skin content appear to decline.

U.S. Pat. No. 7,569,558, entitled, "Topical Delivery of Trace Metals for Skin Care," discloses a method for topical delivery of trace metals for the modulation of certain metalloenzymes. The method of topical delivery of the present invention comprises; (i) mixing of a trace metal salt of a phosphorylated nitrogen heterocyclic base complexed with a chelating agent, and (ii) a carrier, and (iii) topical application of said mixture. The modulation of metalloenzymes such as Superoxide Dismutase, Elastase, Tyrosinase, Matrix metalloproteases, and Ubiquitin-Proteasome pathway by the methods of the present invention is useful for providing anti-inflammatory, skin whitening, wrinkles reduction, skin aging control, cellular antioxidant, acne control, hair growth modulation, and skin damage control benefits.

U.S. Pat. No. 7,855,179, entitled, "Template-Fixed Peptidomimetics with Antimicrobial Activity," discloses Template-fixed β-hairpin peptidomimetics of the general formula (I), wherein Z is a template-fixed chain of 12 α-amino acid residues which, depending on their positions in the chain are Gly or Pro, or of certain types, at least one of these residues being of the type of N-substituted glycines, which types, as the remaining symbols in the above formula, are defined in the description and the claims, and salts thereof, have the property to inhibit the growth of, or to kill microorganisms. They can be used as disinfectants for foodstuffs, cosmetics, medicaments or other nutrient-containing materials or as medicaments to treat or prevent infections. These β-hairpin peptidomimetics can be manufactured by processes which are based on a mixed solid- and solution phase synthetic strategy.

U.S. Pat. No. 8,575,106, entitled, "Cosmetic Uses of Modified Stressed Yeast Extracts and Related Compositions," discloses cosmetic compositions comprising a metal-complexed peptide fraction of stressed yeast extracts and/or a calcium influx inhibitor are disclosed, as well as methods of using such compositions to impart exfoliating, anti-aging, anti-lipid, anti-inflammatory, and/or lightening benefits to the skin; and/or lightening benefits to the hair. These compositions are believed to have modulatory activity against at least one biochemical pathway implicated in skin aging, inflammation, lipid synthesis, and melanin production.

U.S. Pat. No. 8,617,580, entitled, "Compositions for Topical Application Comprising a Peroxide and Retinoid," discloses a composition for topical application comprising as an active ingredient a peroxide and a retinoid wherein one of said peroxide and retinoid is in the form of first microparticles comprising a solid particulate matter of the active ingredient coated by a metal oxide layer and the other of said peroxide and retinoid is present in an uncoated free form or in a coated form of the active ingredient. The invention further relates to method for treating a surface condition in a subject using said composition, a method for preparing a composition exhibiting improved stability, and a kit comprising: (a) a first composition comprising a peroxide as a first active ingredient; and (b) a second composition comprising a retinoid as a second active ingredient; at least one of said first and said second active ingredient being coated by a metal oxide layer.

U.S. Pat. No. 8,674,072, entitled, "Cosmetic and/or Pharmaceutical Composition Comprising a Peptidic Hydrolyzate that can reinforce the Barrier Function," discloses a peptidic hydrolyzate enriched in bioactive peptide, capable of reinforcing the skin barrier function and stimulating epidermal differentiation. Additionally, a cosmetic and/or pharmaceutical composition that includes a physiologically acceptable medium and the peptidic hydrolyzate as the active principle. The cosmetic composition activates the HMG-CoA reductase in the cutaneous cells and treats the cutaneous signs of aging and photo-aging.

SUMMARY OF THE INVENTION

The present invention provides a topical composition for application to a keratinous tissue comprising a cosmetically or pharmaceutically acceptable carrier; one or more selected from potassium, zinc, calcium, rubidium disposed in the cosmetically or pharmaceutically acceptable carrier; and one or more peptides disposed in the cosmetically or pharmaceutically acceptable carrier.

More specifically, the present invention includes 0.01-5% Potassium, 0.01-5% Zinc, 0-1% Calcium, and 0-1% Rubidium in combination with one or more peptides. Alternatively, the present invention includes 0.01-5% Potassium, 0.01-5% Zinc, 0-1% Calcium, and 0-0.5% Rubidium in combination with one or more peptides.

The composition may be potassium, zinc, calcium, and rubidium; potassium and zinc; potassium and zinc and calcium or rubidium; and the one or more peptides are fragments of protein molecules that naturally occur in the skin, e.g., a dipeptide, a tetrapeptide, a hexapeptide, a tripeptide, a pentapeptide, a heptapeptide, an octapeptide, an enneapeptide, or a deca peptide. The one or more peptides may be acetyl hexapeptide-3, e.g., rise 0.05 to 5% argireline. The topical composition may be in the form of a lotion, cream, essence ointment, gel, emulsion, gel pack, cosmetic liquid, ointments, pharmaceuticals, or stick. The composition may include oak bark extract, soy extract, and glycerin. The composition may include a phytoestrogen in a topical composition in the form of an eye cream; a sesame protein in a topical composition in the form of a day cream; a walnut extract in a topical composition in the form of a night cream. The composition may include retinoids, buffering agents, bulking agents, chelating agents, cleansers, colorants, conditioners, diluents, dyes, emollients, fragrances, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, and viscosity modifiers, and/or at least one skin benefit agent selected from the group consisting of astringents, antioxidants, free radical scavengers, anti-acne agents, antimicrobial agents, antifungal agents, chelating agents, anti-aging agents, anti-wrinkle agents, analgesics, skin lightening agents, skin conditioning agents, anti-irritants, anti-inflammatories, anti-cellulite agents, humectants, emollients, organic sunscreens, inorganic sun protecting agents, chemical exfoliating agents, physical exfoliating agent, self-tanning agents, biologically active peptides; and mixtures thereof.

The present invention provides a method for providing a benefit to human skin by providing skin in need of treatment; applying topically to skin a composition comprising an effective amount of one or more selected from potassium, zinc, calcium, and rubidium and an effective amount of a peptide or a homolog thereof having one or more conservative amino acid substitutions, in a cosmetically acceptable vehicle. The composition may be present in an amount sufficient to decrease at least one of melanin synthesis; tumor necrosis factor-α (TNF-α) production; peroxisome proliferator-activated receptors (PPARs) signaling; and metalloproteinase activity; and/or to increase at least one of kallikrein-related peptidases (KLKs) activity; hyaluronic acid production; and collagen synthesis. The skin benefit may be selected from the group consisting of: Treatment or prevention of a sign of skin aging; treatment and/or prevention of fine lines or wrinkles; reduction of skin pore size; improvement in skin thickness, plumpness, and/or tautness; improvement in skin suppleness and/or softness; improvement in skin tone, radiance, and/or clarity; improvement in skin texture and/or promotion of retexturization; improvement in skin barrier repair and/or function; improvement in appearance of skin contours; restoration of skin luster and/or brightness; replenishment of essential nutrients and/or constituents in the skin; improvement of skin appearance decreased by menopause; improvement in skin moisturization and/or hydration; increase in and/or preventing loss of skin elasticity and/or resiliency; improvement in procollagen and/or collagen synthesis; treatment and/or prevention of skin sagging or atrophy; enhancing exfoliation and/or reducing dryness; treatment and/or prevention of skin hyperpigmentation; treatment and/or prevention of inflammation; treatment and/or prevention of excess sebum output; and treatment and/or prevention of cellulite.

The present invention provides a cosmetic composition comprising a physiologically acceptable medium comprising one or more peptides and one or more selected from potassium, zinc, calcium, and rubidium.

The present invention provides a method for treating the cutaneous manifestations of aging and/or photo-aging, the method comprising: providing a composition comprising an effective quantity of a physiologically acceptable topical carrier comprising one or more peptides, and one or more selected from potassium, zinc, calcium, and/or rubidium.

The present invention provides a method for down regulating the production of one or more proteases in a keratinous tissue comprising the steps of: providing a composition comprising an effective quantity of a physiologically acceptable topical carrier, comprising one or more peptides and one or more selected from potassium, zinc, calcium, and/or rubidium, wherein the composition down regulates the production of one or more proteases. The one or more proteases may be matrix metalloproteases or associated with the breakdown of collagen and tissue in the skin.

The present invention provides a topical composition for application for stimulates synthesis of collagen I, IV, VII, XVII and nidogen I proteins comprising a cosmetically or pharmaceutically acceptable carrier; one or more selected from potassium, zinc, calcium, rubidium disposed in the cosmetically or pharmaceutically acceptable carrier; and one or more peptides disposed in the cosmetically or pharmaceutically acceptable carrier sufficient to stimulate synthesis of collagen I, IV, VII, XVII or nidogen I proteins.

The present invention provides a topical pharmaceutical composition for application to a keratinous tissue comprising a pharmaceutically acceptable carrier; one or more selected from potassium, zinc, calcium, rubidium disposed in the pharmaceutically acceptable carrier; and one or more peptides disposed in the pharmaceutically acceptable carrier.

The present invention provides a topical pharmaceutical composition and methods to aid in wound healing, tissue regeneration and/or tissue remodeling of a keratinous tissue comprising a pharmaceutically acceptable carrier; one or more selected from potassium, zinc, calcium, rubidium disposed in the pharmaceutically acceptable carrier; and one or more peptides disposed in the pharmaceutically acceptable carrier.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the phrase "active ingredient" refers to an ingredient having a therapeutic, cosmetic or cosmeceutical effect.

By the term "pharmaceutical active agent" we include any compound, including pharmaceutical acceptable derivatives such as a salt, solvate and pro-drug and any composition which may be used for the curative and/or prophylactic treatment of a medical condition of a human or animal. Preferably, the pharmaceutical active agent possesses antibacterial, antiviral and/or antifungal activity. More preferably, the pharmaceutical active agent comprises an antibacterial agent.

As used herein, the phrase "topical application" refers to an application on the skin, hair, ears, mucous membranes, rectal application, and nasal application, as well as dental or gum application within the oral cavity.

As used herein, "peptide" refers to any composition that includes two or more amino acids joined together by a peptide bond. Peptides may be about 2 to about 200 amino acids or more in length, and generally correspond to a fragment of a full-length protein, where the fragment does not include all the amino acids of the native full-length protein. In some embodiments, the peptide may be from at least about 3, at least about 4, at least about 5, at least about 6, at least about 8, at least about 10, at least about 15, or at least about 20 amino acids in length. In some embodiments, the peptide may be no more than about 200, no more than about 100, no more than about 50, no more than about 30, or no more than about 20 amino acids in length. For example, in some embodiments, the peptide includes less than about 20 amino acids, less than about 15 amino acids, less than about 10 amino acids, or about six amino acids. It further will be appreciated that peptides may contain amino acids other than the 20 amino acids commonly referred to as the 20 naturally-occurring amino acids, and that many amino acids, including the terminal amino acids, may be modified in a given peptide, either by natural processes such as glycosylation and other post-translational modifications, or by chemical modification techniques, such as those well known in the art. Among the known modifications which may be present in peptides of the present invention include, but are not limited to, acetylation, acylation, ADP-ribosylation, amidation, branching, cross-linking, cyclization, disulfide bond formation, demethylation, glycosylation, hydroxylation, iodination, methylation, oxidation, phosphorylation, prenylation, racemization, selenoylation, sulfation, and ubiquitination.

As used herein, "amount effective" or an "effective amount" to provide a particular benefit to the skin refers to the active amount of the composition, including potassium, zinc, calcium, rubidium, or a combination thereof, and one or more peptides, sufficient to provide a clinically measurable improvement in the particular manifestation of skin when applied for a sufficient time.

As used herein, "wrinkle" or "wrinkling" refers to both fine wrinkling and/or coarse wrinkling. Fine wrinkling or fine lines refers to superficial lines and wrinkles on the skin surface. Coarse wrinkling refers to deep furrows, particularly deep lines/wrinkles on the face and around the eyes, including expression lines such as frown lines and wrinkles, forehead lines and wrinkles, crow's feet lines and wrinkles, nasolabial folds, and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth.

As used herein "collagen" is used interchangeably with "collagen I" or "collagen type I," the type present in skin as a dermal matrix component. Collagen I is composed of three protein chains wound together in a tight triple helix, which provides a tensile strength greater than that of steel. It is created by fibroblasts, specialized skin cells located in the dermis. Formation involves the production of preprocollagen I by ribosomes along the rough endoplasmic reticulum (RER); conversion to procollagen I and formation of the triple helical structure within the RER; and eventual formation of tropocollagen outside the cell, the form that aggregates to give collagen fibrils and then fibers. Collagen gives skin firmness, strength, durability, and a youthful smooth, plump appearance.

The present invention provides a composition that includes potassium, zinc, calcium, rubidium or a combination thereof and one or more peptides for use in wound care, e.g., chronic wounds. Chronic wounds are generally defined as wounds that have not healed after thirty days of consistent clinical treatment, and include diabetic ulcers, burns, pressure ulcers (bedsores), and venous stasis ulcers. One embodiment includes an oak bark extract which down regulates the production of certain proteases and matrix metalloproteases, or MMPs, which are protein enzymes that are proven to impede the healing of a majority of chronic wounds. Approximately 80% of chronic wounds display elevated levels of proteases (including MMPs), which impede or stop the wound-healing process.

The present invention provides a composition that includes potassium, zinc, calcium, rubidium, or a combination thereof, and one or more peptides for use in reducing the signs of aging and appearance of wrinkles. Facial wrinkling associated with aging is caused and exacerbated by numerous factors. Beyond the physiological pathways, molecular mechanisms involved in facial aging include changes in collagen conformation, elastin polypeptide degradation, and problems of the skin lipid matrix. The present invention provides a cosmeceutical composition that includes potassium, zinc, calcium, rubidium, or a combination thereof, and one or more peptides, for use in reducing the signs of aging and appearance of wrinkles. The present invention is effective in controlling a group of proteases and other enzymes associated with the breakdown of collagen and tissue in the skin. The breakdown of collagen is a key factor in the aging of skin. Proteases have recently been identified as a contributing factor affecting aging skin by destroying the collagen in the dermis. Protease activity began at the cellular level in the dermis in the 21 to 40 age group. The activity became very high in the 41 to 60 age group resulting in a greatly reduced level of collagen. Recent studies also establish that changes can be significantly reduced by inhibiting soluble N-ethylmaleimide-sensitive factor attachment protein receptor (SNARE) complex formation, a core of membrane proteins that mediate neuronal exocytosis. Their inhibition by short synthetic peptides, used in the instant composition, can decrease facial wrinkle formation and aging. The overproduction and release of cate-cholamines and encouraged the formation of wrinkles and fine lines. Current compositions include a day cream, a night cream, an eye cream, plus a product for post Retin-A or laser repair usage, which is a PEG-based wound and burn formula containing the present invention. This composition is extremely beneficial when used with exfoliating products and laser repair, with studies showing greater than a 50% improvement in healing time.

Clinical trials of the composition that includes potassium, zinc, calcium, rubidium, or a combination thereof, and one or more peptides were conducted in High Point, N.C., under the direction of Dr. Zoe Draelos. Fifty women participated in the test, with forty testing the active product against a placebo (a very good botanical base), and 10 testing the product against a cold cream-type placebo. The trials were double-blind. Each woman used one cream (an active or a placebo) on each side of her face, and neither Dr. Draelos nor the participant knew which was the active cream. At the beginning of the study and at mid-point, each participant was interviewed, photographed and visually examined, each side of her face tested for skin moisture, and skin conductivity, and a small silicone mask taken from each side of her face. Each woman turned in unused product (which was weighed) and a diary of her experience. Dr. Draelos made very positive comments about the product in her report, and results were dramatic, particularly over the first six weeks. Essentially all participants wanted more skin cream at the end of the study (which was provided), and all felt the moisturizing quality of the cream was outstanding.

Aging of the facial skin is a ubiquitous condition ultimately affecting all women worldwide. It is due to extrinsic and intrinsic factors. It appears that both extrinsic and intrinsic aging are due to the secretion of metalloproteases (MMP) such as collagenase (collagenase-1, MMP-1) and gelatinase (gelatinase A, MMP-2). Collagenases cleave the triple helical domain of fibrillar collagens at a neutral pH and are produced following less than 10 minutes of UVA radiation exposure. The collagenase breaks down the fibrillar collagens present in the dermis resulting in the appearance of wrinkles that contribute to an aged facial appearance. The study objective was to evaluate the efficacy of a topical MMP regulator in facial skin aging. This was a 6-week double-blind, split-face, vehicle-controlled randomized study with a four week extension. One group of 20 subjects applied the vehicle 1 to the left face and the active to the right face. The second group of 20 subjects applied the active to the left face and the vehicle 1 to the right face. A third group of 5 subjects applied the active to the left face and vehicle 2 to the right face. And, a fourth group of 5 subjects applied the vehicle 2 to the left face and the active to the right face. Both products were applied twice daily. Subjects had mild to moderate aging as assessed by the dermatologist investigator. Investigator and subject visual facial assessments, noninvasive assessments and photography were performed at all evaluation time points (weeks 0, 2, 4, 6 and the 10 week extension). Forty female subjects 25 to 65 years-of-age who met the inclusion and exclusion criteria were enrolled. An additional 10 subjects were added to test a second vehicle formulation. The following items represented the inclusion criteria: Females; Ages 25 to 65; subjects must have mild to moderate facial aging; subjects must be in general good health as determined from a medical history; subjects must be willing not to change any of their skin care products or facial cosmetics for the duration of the study; subjects must read and sign the informed consent form after the nature of the study has been fully explained; subjects who are using hormones or oral contraceptives must have used them for more than 3 months prior to study enrollment and must not discontinue their use during the study. The following represented the exclusion criteria: Subjects with known allergies or sensitivities to ingredients contained in the test products; subjects who are required to spend excessive time in the sun (i.e. lifeguards, other outdoor workers); subjects who are pregnant or nursing or planning to become pregnant during the course of the study; subjects who are currently participating or have participated within the last 4 weeks in any other clinical study (i.e., dermal patch, use tests, investigational drug or devices, etc.); subjects viewed by the investigator as not being able to complete the study. All subjects remained on any oral or topical medications unchanged in type or dose during the 6-week study period and the 4-week extension period. Subjects were evaluated by collecting a variety of observations at weeks 0, 2, 4, and 6 of the study, as well as the 10-week extension. The same trained evaluator at each study facility performed all visual assessments whenever possible. The parameters to be evaluated were: Overall Aging Assessment: Each side of the face was evaluated separately for aging based on the following 5-point ordinal grading scale: 0=None, 1=Slight, 2=Mild, 3=Moderate, 4=Severe; Investigator Visual Evaluations: Periorbital wrinkling, erythema, pigmentation irregularities, skin roughness, scaling, and itching were graded using the 5-point scale: 5-point grading scale 0=None 1=Slight 2=Mild 3=Moderate 4=Severe; Subject Assessment: Subjects completed a questionnaire at each visit regarding stinging, skin roughness, and skin wrinkling; Noninvasive Assessments: Subjects had TEWL measurements and pin probe corneometry performed at each visit from the right and left forehead. Profilometry was performed from both cheeks at baseline and at week 6 and at the week 10 extension; Digital Photography: Subjects had digital photography performed at baseline and weeks 0, 2, 4, and 6 of the study. Photographs were also obtained at the week 10 extension visit. The digital photography consisted of frontal, right, and left facial images of the subject with the head placed in a three-point restraining mount. Subjects applied the products 2 times daily, morning and evening. Compliance was determined from the diary sheets. Review of the diary sheets indicated excellent subject compliance such that no data required disqualification. A study termination form was completed for each study subject who receives study product. All subjects completed week 6. Four subjects in the active/vehicle 1 group elected to not complete the week 10 extension and 2 subjects in the active/vehicle group elected not to complete the week 10 extension. The study products consisted of an active MMP regulator as compared to vehicle 1 without the MMP regulator and vehicle 2 without the MMP regulator and the selected botanical additives. The study product was stored at room temperature in a locked, limited access area at the study site. All bottles of both study active and vehicle were returned by all subjects. Selected samples were returned to the sponsor and the remainder of the returned product and unused vehicle was destroyed. No serious adverse reactions occurred, however many subjects reported both eye stinging and facial stinging associated primarily with the active. This data was captured and is reported under the data analysis. The sponsor was notified of the stinging associated with study products after the week 2 visit and it was elected by the investigator and the sponsor to complete the study despite the incidence of stinging. The statistical evaluation of the data was performed by Dermatology Consulting Services utilizing a Mann Whitney nonparametric two-tailed paired test. A sample size of forty subjects was chosen by the sponsor as sufficient to obtain the split face needed for evaluation of the active versus the vehicle 1. At the request of the sponsor, 10 additional subjects were added to evaluate the active versus vehicle 2. Patients were assigned with a computer generated randomization schedule to apply the active or the vehicle 1 or 2 to the right or left face. Significance was defined at the $p=0.05$ or less level based on a two-sided test. Patient demographic and baseline evaluations were compared to determine that the 4 groups were properly balanced. Statistical analysis revealed equal balancing of subject findings within the 4 groups. Several protocol modifications were made based on the wishes of the sponsor. The study was extended to add 10 subjects to test an additional vehicle 2 without the botanical additives. Additionally, the study was extended to 10 weeks to allow for collection of additional data. Investigator Assessment Active/Vehicle 1. This data set was particularly challenging due to the excellent moisturizing characteristics of vehicle 1. Statistical superiority ($p=0.015$) of the active over vehicle 1 was achieved at week 6 in the overall investigator assessment. The data sets were well balanced as indicated by the excellent matching of the skin characteristics at baseline. Little difference between the active and vehicle 1 groups could be appreciated at week 2, probably due to the moisturizing benefits that were present in both comparative products that typically manifest after 14 days of use. There was a trend for the investigator to prefer the active product both at week 2 and week 4. This trend became statistically significant at week 6, but the trend was lost at week 10. Subjects reported much less stinging at week 10 and a noticeable change in the active product smell and appearance. Could the active agent have degraded in the 10-week product? Also, the vehicles began to thicken and perhaps a more concentrated moisturizer benefit was delivered to the skin surface. The weather cooled dramatically between weeks 6 and 10, which may have also influenced the study by increasing the apparent moisturizing effect of vehicle 1. Investigator Assessment Active/Vehicle 2. Vehicle 2 did not perform as well as vehicle 1, thus allowing better separation from the active. Again, the groups were well balanced at baseline, but only 10 subjects were present in this group accounting for the challenging statistics. There was a clear preference for active over vehicle 2 at all time points that reached statistical significance in terms of skin scaling (p=0.041) and skin roughness (p=0.045) at week 10. The overall evaluation almost reached statistical significance (p=0.065), but this was prevented by the limited data points as this arm of the study was powered too low. Subject Assessment Active/Vehicle 1. The subjects were unable to distinguish any skin benefits in terms of improvement in skin wrinkling and roughness between the active and vehicle 1. This may have been due to the excellent moisturizing qualities of both products that the subjects could not discern. However, there was a statistically significant increase in skin stinging for the active over vehicle 1 at all time points (weeks 2, 4, 6, and 10) with the biggest difference occurring at week 6. Subject Assessment Active/Vehicle 2. The subjects were unable to distinguish any difference in terms of improvement in skin wrinkling and roughness between the active and vehicle 2. There was no statistically significant difference between active and vehicle 2 in terms of stinging. However, the active did receive higher stinging scores than vehicle 2. This may be due to the small number of subjects enrolled in this arm of the study. Trans epidermal water loss (TEWL) Assessment Active/Vehicle 1. This data revealed that both the active and vehicle 1 were excellent moisturizers that did not damage cutaneous barrier function. TEWL Assessment Active/Vehicle 2. This data revealed that both the active and vehicle 2 were excellent moisturizers that did not damage cutaneous barrier function. Corneometry Assessment Active/Vehicle 1. The data demonstrated that skin hydration was not altered by either the active or vehicle 1. Corneometry Assessment Active/Vehicle 2. This data demonstrated that skin hydration was not altered by either the active or vehicle 2. The replicas were analyzed by CuDerm Corporation. The data that was returned was quite extensive. The data is broken into two sets labeled N and P. N represents the appearance of the major wrinkles around the eyes characterized as crow's feet and the P represents the appearance of the minor fine lines around the eyes. N stands for normal and P stands for parallel to indicate the direction of the light as it illuminates the specimen to digital image analysis. The data has been presented at each evaluation time point consisting of baseline, week 6, and week 10 for both the active vs. placebo 1 and active vs. placebo 2. The data charts comparing active vs. placebo 1 at week 6 show a statistically significant value (P=0.021) in terms of wrinkle breadth, but the smaller number in the placebo 1 column indicates that smaller wrinkles were produced by the placebo 1 over the active. This is also the case for the one statistically significant point in number of wrinkles at week 10 where placebo 1 again outperformed the active. There were no statistically significant points for placebo 2, which is expected since placebo 1 outperformed placebo 2 in all other analyses. The P analysis of the replicas failed to reveal any statistically significant endpoints. Photography Analysis. This analysis of the baseline versus the week 10 photographs of both sides of the face to compare the active with vehicle 1 revealed no statistically significant difference. There was also no statistically significant difference between vehicle 2 and the active. The photographs were consistent and illustrative, but were hard to evaluate in a blinded fashion. Based on the data analysis: It appears that the MMP regulator active underwent some degradation during the 10-week run time of the study. Both a darkening of the color of the active and an odor were noted as the subjects used the product. It is believed that the genestein in the active was oxidizing accounting for both the color change and the odor. This means that more and better antioxidants should be incorporated into the formulation. The MMP regulator active also thickened during the course of the study. Both vehicle 1 and vehicle 2 experienced thickening. The primary efficacy endpoint was the statistically significant (p=0.05 or less) improvement in facial aging as assessed by the dermatologist investigator favoring active over vehicle. This efficacy endpoint was achieved at the end of week 6 in terms of overall investigator assessment for the active/vehicle 1 group. It was also achieved for the vehicle/active 2 group at week 10 for improvement in skin roughness and decreased skin scale. The secondary efficacy endpoint was the statistically significant (p=0.05 or less) improvement in skin condition as assessed by the subjects showing a preference for active over vehicle. This efficacy endpoint was not achieved. There was a statistically significant increase in stinging with active over vehicle 1, however; this means that the active contained an ingredient that produced cutaneous stinging. The tertiary efficacy endpoint was the statistically significant (p=0.05 or less) improvement in profilometry, TEWL, corneometry, or photography favoring active over vehicle. This endpoint was not met in terms of TEWL or corneometry.

The present invention provides a composition that includes potassium, zinc, calcium, rubidium, or a combination thereof, and one or more peptides. One embodiment includes water and glycerin and hesperidin methyl chalcone and steareth-20 and dipeptide-2 and palmitoyl and tetrapeptide-3. In one embodiment, the composition includes Acetyl hexapeptide-3 or a derivative or portion thereof, including Argireline i.e., (6S,9S,12S,15S,18S,21 S)-21-Acetamido-1-amino-12-(3-amino-3-oxopropyl)-6-carbamoyl-18-(2-carboxyethyl)-9-(3-guanidinopropyl)-1-imino-15-(2-(methylthio)ethyl)-8,11,14,17,20-pentaoxo-2,7,10,13,16,19-hexaazatetracosan-24-oic acid.

The one or more peptides of the present invention include unique new peptide that both reduces the degree of existing facial wrinkles and has been demonstrated effective against their development. It's been shown to inhibit the formation of the SNARE complex as well as catecholamine release. These inhibitions confer anti-aging activity on the one or more peptides including Argireline are closely related to the basic biochemical mechanisms of wrinkle formation. Controlled studies have also demonstrated that facial wrinkle depth can be reduced, especially in the forehead and around the eyes, and that the one or more peptides including Argireline can prevent apparent facial skin aging. Skin topographic analysis performed on healthy female volunteers confirmed the validation of the proposed biochemical mechanism of action. Facial wrinkling associated with aging is caused—and exacerbated—by many factors. Beyond the physiological pathways, molecular mechanisms involved in facial aging include changes in collagen conformation, elastin polypeptide degradation, and problems of the skin's lipid matrix. Recent studies clearly establish that these changes can be significantly reduced by inhibiting SNARE complex formation, a core of membrane proteins that mediate neuronal exocytosis. Their inhibition by short synthetic peptides can decrease facial wrinkle formation, and thereby the appearance of aging. The overproduction and release of catecholamines also encourages the formation of wrinkles and fine lines.

Argireline's specific sequence was discovered within a combinatorial library of hexapeptides and shown to inhibit the SNARE complex formation and catecholamine release. Once identified, it was synthesized by solid phase peptide synthesis and then purified and characterized. Argireline solution was found to inhibit vesicle docking by preventing formation of the essential ternary SNARE Complex. Inhibition of noradrenaline and adrenaline release was also demonstrated in a second in vitro study. In vivo tests further demonstrated the benefits of Argireline solution. Facial topography analysis (for measuring the effectiveness of an ONV emulsion containing 10% Argireline solution) was performed using silicon replicas from around the eyes at 0, 15, and 30 days of a twice-a-day treatment regimen. Analyses of the imprints were performed by confocal laser scanning microscopy. It was observed that the severity of wrinkles around the eyes decreased up to 17% after 15 days of treatment and up to 27% after 30 days of treatment, substantiating the proposed biochemical mechanism hypothesis. The anti-wrinkle effect of Argireline solution was ascertained in two different in vitro tests directly related to the formation of wrinkles in the epidermis as well as a separate in vivo test performed on healthy human volunteers. SNARE complex modulation in chromaffin cells. This test evaluates inhibition of the SNARE complex formed by peptides from the N-terminus of SNAP-25 (synaptosome-associated protein of 25 kDa). Argireline solution modulates SNARE complex formation at concentrations in the mM range. Chromaffin cells were prepared and further separated from erythrocytes and other impurities by centrifugation gradient. Cells were maintained in monolayer cultures. The ternary SNARE complex was precipitated and incubated with Argireline and other related peptides, or without them (as a control) Immunocomplexes were analyzed under non-reducing conditions and immunoblotted with an anti-syntaxin mAb. Argireline proved to modulate vesicle docking by attenuating the formation of the essential ternary SNARE complex. Modulation of catecholamine release in chromaffin cells. Inhibition of the release of catecholamines was determined by monitoring the neurotransmitters adrenaline and noradrenaline. Chromaffin cells were incubated with tritiated noradrenaline/adrenaline and Argireline. The release of catecholamines, as well as the total cell content, was determined by liquid scintillation counting. The significant modulation of both neurotransmitters at nM concentrations of Argireline solution is a clear indicator of the potent anti-wrinkle activity of this hexapeptide. Determination of efficacy against facial wrinkling. An independent study of the effect of Argireline solution on the elasticity of the skin around the eyes was performed. Using silicone facial replicas and confocal microscopic analysis, the researchers measured changes in the depth of skin wrinkling. The skin replicas show the improvement in facial smoothness at 15 and 30 days post-Argireline treatment, compared with the results obtained without the incorporation of Argireline solution into the test cream. The researchers concluded that Argireline solution reduced the depth of wrinkles up to 17% after 15 days and 27% following 30 days of treatment. Human dermal fibroblasts. The test was conducted on human dermal fibroblasts at concentrations between 10 µg/ml and 1 mg/ml with a cell density of 21,000 cell/cm2. No signs of cytotoxicity were observed. Human epidermal keratinocytes. The test was carried out on human epidermal keratinocytes at concentrations between 10 µg/ml and 1 mg/ml with a keratinocyte density of 15,000 cell/cm2. The results showed no signs of cytotoxicity at the concentrations assayed. Argireline can be incorporated in cosmetic formulations such as emulsions, gels, sera, etc., where the reduction in deep lines or wrinkles in the forehead or around the eyes area is desired. The recommended dosage of Argireline is 5%. The present invention provides a composition that includes potassium, zinc, calcium, rubidium or a combination thereof and one or more peptides, wherein the one or more peptides include Argireline at about 0.05 to 5%.

The present invention provides a composition that includes potassium, zinc, calcium, rubidium or a combination thereof and one or more peptides and is based on extensive clinical trials and pharmaceutical technology. When it is applied to the skin, it significantly reduces wrinkles due to aging and other skin conditions. In addition to having a family of additional active ingredients for rapid as well as long-lasting effect. Each of the compositions incorporate active ingredients particular to that product's usage. The other active ingredients help prevent the degrading action of natural skin aging. The skin cream base is the finest combination of botanicals and moisturizers available today, as verified by double-blind clinical trials.

The present invention provides a composition that includes potassium, zinc, calcium, rubidium, or a combination thereof, and one or more peptides; helps reduce the breakdown of collagen, laminin, elastin, and other components of the skin. The present invention provides a composition that includes potassium, zinc, calcium, rubidium, or a combination thereof, and one or more peptides, and has found age-related changes in the activity of these enzymes, and can reduce skin degradation and loss of skin tone, enhance growth factors, regulate MMPs, and reduces inflammation.

The present invention provides a composition that includes potassium, zinc, calcium, rubidium, or a combination thereof, and one or more peptides. In general the one or more peptides are tiny fragments of protein molecules: Short chains of amino acids that naturally occur in the skin. Peptides can allow the natural production of collagen and elastin, both of which plump the skin and give it elasticity. The composition can further comprise oak bark extract, soy extract, and glycerin for a synergistic effect to enhance the stratum corneum to increase hydration, which in turn helps allow the natural production of collagen.

In the day and night creams a proprietary peptide is used to provide a protective effect against photo-induced aging, and it significantly stimulates synthesis of collagen I, IV, VII, XVII and nidogen I proteins. While these proteins of the dermis and dermal-epidermal junction usually decrease with age, rejuvenates the dermal structure causing aging skin to behave like younger skin.

Soy Extract including phytoestrogen is used in the day and night cream. This molecule mimics the body's natural estrogen and contributes to the skin's softness and suppleness, much as natural estrogen does, without the drawbacks of estrogen.

In an eye cream formulation the composition that includes potassium, zinc, calcium, rubidium, or a combination thereof, and one or more peptides, are effective in diminishing darkness and puffiness around the eyes and general skin discoloration. Poor circulation and capillary fragility are primary factors that exacerbate the appearance of under-eye circles.

In a day cream formulation the composition that includes potassium, zinc, calcium, rubidium, or a combination thereof, and one or more peptides, further includes sesame protein is a skin-tightening agent that visibly smooth the skin and is a very effective base for application of make-up. Sun-screen may also be added to the day product.

In a night cream formulation the composition that includes potassium, zinc, calcium, rubidium or a combination thereof and one or more peptides further comprising walnut extract provides the skin with phytic acid, polyphenols, proteins, mineral salts, and vitamins. This protects the cell's antioxidant pool and has biostimulating properties while shielding from the consequences of oxidative stress. The walnut extract provides substantiated effects on extrinsic aging by reduced apoptosis and the inflammation processes.

The present invention provides a composition that includes potassium, zinc, calcium, rubidium or a combination thereof and one or more peptides and Retin-A. The Retin-A products have at least 4 different dosage levels, ranging from 0.075% to 0.5%. The low dose acts well for the stimulation of the cellular activity but does not produce a strong inflammatory reaction. This is a great product for a broad spectrum of users, from younger to older.

The present invention provides a composition that includes potassium, zinc, calcium, rubidium or a combination thereof and one or more peptides for the treatment of rosacea. The composition can be in the form of a kit that includes the composition, a skin cleanser, day cream, a night cream, and eye soufflé for the rosacea-affected market.

Another aspect of the instant invention relates to cosmetic use of compositions including potassium, zinc, calcium, rubidium or a combination thereof and one or more peptides. The cosmetic compositions surprisingly act to increase one or more of KLKs activity, hyaluronic acid production, and collagen synthesis; and/or to decrease one or more of metallocollagenase activity, PPARs signaling, TNFα production, and melanin synthesis, and accordingly find use in exfoliating, anti-aging, anti-lipid, anti-inflammatory, and/or skin (or hair) lightening products.

In some embodiments, a method for providing at least one benefit to human skin is provided, where the method comprises topically applying to skin in need thereof at least one composition described herein in a cosmetically acceptable vehicle. The composition will comprise an effective amount of a composition including potassium, zinc, calcium, rubidium, or a combination thereof, and one or more peptides.

The compositions of the invention can be applied to skin in need of treatment, such as skin which suffers from a deficiency or loss in any of the foregoing attributes or conditions, or which would otherwise benefit from the composition's exfoliating, anti-aging, anti-lipid, anti-inflammatory and/or skin lightening effects, e.g., as described herein. For example, the composition including potassium, zinc, calcium, rubidium, or a combination thereof, and one or more peptides, can be provided in a cosmetically acceptable vehicle, topically applied to a desired area of skin, and allowed to remain on the area in an amount effective to treat and/or prevent an unwanted feature or condition of the skin, and/or to improve the aesthetic appearance of the skin.

In certain preferred embodiments, the cosmetic compositions described herein can be used to treat and/or prevent signs of skin aging or other skin damage. Signs of skin aging include any dermatological signs of aging, including signs caused by intrinsic aging, or caused by extrinsic factors. The compositions may be applied to skin already showing visible signs of aging, or likely to show such signs, e.g., due to age or sun exposure.

An early sign of skin aging involves the gradual development of facial wrinkles, whether fine surface lines or deeper creases and folds. While wrinkling and other signs of aging are intrinsic to skin, the process may be accelerated by external factors, such as excessive exposure to the sun and other damaging elements, overactive facial expression muscles, frequent use of tobacco products, poor nutrition, or certain skin disorders. Fine surface lines that progress to deeper creases, deepening facial wrinkles due to repeated skin folding, and deep folds that develop with maturity are visible changes associated with aging.

Treating signs of skin aging refers to eradicating, reducing, ameliorating, or reversing one or more of the unwanted features associated with skin aging, e.g., by reducing loss of skin firmness or plumpness to a perceptible extent. For example, compositions and methods of the instant invention may be used to reverse or treat signs of skin aging once manifested. Preventing signs of skin aging refers to affording skin a benefit that serves to avoid, delay, forestall, or minimize one or more unwanted features associated with aging, e.g., by slowing the loss of firmness or plumpness as the skin eventually ages. That is, the compositions and methods of the instant invention may be employed prophylactically, e.g., to forestall signs of skin aging in individuals that have not yet manifested signs of skin aging, most commonly in individuals under 25 years of age.

Compositions used to as anti-aging agents will comprise an effective amount of a composition including potassium, zinc, calcium, rubidium or a combination thereof and one or more peptides to treat and/or prevent signs of aging. Some particularly preferred embodiments provide compositions for topical application which comprise an effective amount of composition including potassium, zinc, calcium, rubidium or a combination thereof and one or more peptides to treat and/or prevent signs of aging. Treatment and/or prevention generally results in an improvement in one or more unwanted features and/or in the overall aesthetic appearance of the treated skin.

In certain embodiments, the cosmetic compositions described herein can be used to treat and/or prevent signs of skin aging or other skin damage. Signs of skin aging include any dermatological signs of aging, including signs caused by intrinsic aging, or caused by extrinsic factors. The compositions may be applied to skin already showing visible signs of aging, or likely to show such signs, e.g., due to age or sun exposure.

An early sign of skin aging involves the gradual development of facial wrinkles, whether fine surface lines or deeper creases and folds. While wrinkling and other signs of aging are intrinsic to skin, the process may be accelerated by external factors, such as excessive exposure to the sun and other damaging elements, overactive facial expression muscles, frequent use of tobacco products, poor nutrition, or certain skin disorders. Fine surface lines that progress to deeper creases, deepening facial wrinkles due to repeated skin folding, and deep folds that develop with maturity are visible changes associated with aging.

Treating signs of skin aging refers to eradicating, reducing, ameliorating, or reversing one or more of the unwanted features associated with skin aging, e.g., by reducing loss of skin firmness or plumpness to a perceptible extent. For example, compositions and methods of the instant invention may be used to reverse or treat signs of skin aging once manifested. Preventing signs of skin aging refers to affording skin a benefit that serves to avoid, delay, forestall, or minimize one or more unwanted features associated with aging, e.g., by slowing the loss of firmness or plumpness as the skin eventually ages. That is, the compositions and methods of the instant invention may be employed prophylactically, e.g., to forestall signs of skin aging in individuals that have not yet manifested signs of skin aging, most commonly in individuals under 25 years of age.

Compositions used to as anti-aging agents will comprise an effective amount of a composition including potassium, zinc, calcium, rubidium, or a combination thereof, and one or more peptides, to treat and/or prevent signs of aging. Some particularly preferred embodiments provide compositions for topical application which comprise an effective amount of composition including potassium, zinc, calcium, rubidium, or a combination thereof, and one or more peptides to treat and/or prevent signs of aging. Treatment and/or prevention generally results in an improvement in one or more unwanted features and/or in the overall aesthetic appearance of the treated skin.

The improvement in the unwanted feature and/or overall aesthetic appearance can include one or more of the following: Reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing skin atrophy; improving skin tone, radiance, and/or clarity; preventing, reducing, and/or ameliorating skin sagging; improving skin firmness, plumpness, tautness, suppleness and/or softness; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause, such as essential nutrients or other skin constituents; ameliorating the effects of estrogen imbalance; improving communication among skin cells; increasing cell proliferation and/or multiplication; increasing skin cell metabolism decreased by aging and/or menopause; retarding cellular aging; improving skin moisturization and/or hydration; enhancing skin thickness; increasing skin elasticity and/or resiliency; improving procollagen and/or collagen synthesis; enhancing exfoliation; improving microcirculation; reducing dryness; and any combinations thereof.

In certain preferred embodiments, the compositions and methods of the invention are directed to the treatment and/or prevention of fine lines or wrinkles in the skin. In the case of treatment, the compositions are applied to skin in need of such treatment, by which is meant skin having wrinkles and/or fine lines. The fine lines and/or wrinkles may occur on any surface of the skin, including without limitation, the skin of the hands, arms, legs, neck, chest, and face, including the forehead. Preferably, the compositions are applied directly to the fine lines and/or wrinkles. For example, methods for treating fine lines and wrinkles may comprise topically applying a composition described herein to skin in need thereof, e.g., topically applying directly to a fine line and/or wrinkle in an amount and for a time sufficient to reduce the severity of the fine lines and/or wrinkles. The effect of a composition on the appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

In certain embodiments, the compositions and methods of the instant invention are directed to improving skin firmness, plumpness, and/or tautness. In certain embodiments, the compositions and methods of the instant invention are directed to increasing and/or preventing loss of skin elasticity. Elasticity of skin refers to the skin's springiness and/or resilience, due to the skin's ability to regain its original shape and size after deformation.

Loss of firmness, wrinkling and other signs of aging result in part from loss of skin collagen over time. As used herein, "increasing collagen synthesis" and related expressions refer to stimulating, inducing, or up-regulating procollagen and/or collagen production to increase the collagen content in an area of skin, preferably improving skin firmness and/or plumpness to a perceptible extent. For example, in some embodiments, collagen synthesis is increased by at least about 10%, at least about 25%, at least about 50%, at least about 75%, or at least about 90%, compared to the synthesis of collagen in the absence of the composition. The extent of collagen and/or collagen synthesis in the skin can be determined by appropriate assays, e.g., in vitro assays described herein or known in the art.

In certain embodiments, the compositions of the instant invention including potassium, zinc, calcium, rubidium, or a combination thereof, and one or more peptides in an amount sufficient to decrease metalloproteinase activity in given area of skin when topically applied thereto.

Loss of hyaluronic acid over time also plays a role in skin aging. Hyaluronic acid is a glycosaminoglycan (GAG) found in the skin as part of the ECM. GAGs are long unbranched polymers of repeating disaccharide units, mainly composed of hexosamine, hexose, hexuronic acid moieties, or sulfates thereof. GAGs bind to proteins in the skin to form proteoglycans, which contribute to the growth, preservation, and repair of skin. Hyaluronic acid, in particular, has been reported to be responsible for hydration of the skin, nutrient exchange, and protection against free radicals.

In certain preferred embodiments, the compositions and methods of the instant invention are directed to improving skin moisturization and/or hydration. For example, in certain embodiments, the compositions of the instant invention including potassium, zinc, calcium, rubidium, or a combination thereof, and one or more peptides in an amount sufficient to increase hyaluronic acid production in a given area of skin when topically applied thereto. As used herein, "increasing hyaluronic acid production" and related expressions refer to stimulating, inducing, or up-regulating hyaluronic acid synthesis to increase the hyaluronic acid content in an area of skin, preferably improving skin hydration and/or resiliency by a perceptible amount. For example, in some embodiments, hyaluronic acid production is increased by at least about 10%, at least about 25%, at least about 50%, at least about 75%, or at least about 90%, compared to the production of hyaluronic acid in the absence of the composition. The extent of hyaluronic acid and/or hyaluronic acid production in the skin can be determined by appropriate assays, e.g., in vitro assays described herein or known in the art.

In some embodiments, a composition described herein is topically applied to the skin of the elbows, knees, ankles, feet, soles of the feet, heels, and the like, areas. In some preferred embodiments, a composition described herein is topically applied an area of dry skin.

In some embodiments, the cosmetic compositions for treating and/or preventing signs of skin aging can further comprise additional exfoliating and/or anti-aging agents. For example, the cosmetic composition comprising potassium, zinc, calcium, rubidium or a combination thereof and one or more peptides in an amount effective to treat and/or prevent signs of skin aging. It is contemplated that synergistic improvements may be obtained with such combinations, in some embodiments.

Exemplary exfoliating agents include, without limitation, alpha-hydroxyacids, beta-hydroxyacids, oxaacids, oxadiacids, and their derivatives such as esters, anhydrides, and salts thereof. Suitable hydroxy acids include, for example, glycolic acid, lactic acid, malic acid, tartaric acid, citric acid, 2-hydroxyalkanoic acid, mandelic acid, salicylic acid, and derivatives thereof, as well as fruit enzymes, such as pineapple enzyme. A preferred additional exfoliating agent is glycolic acid.

Exemplary anti-aging agents include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; antioxidants, exfoliating agents (e.g., glycolic acid, 3,6,9-trioxaundecane-dioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; anti-aging botanicals, keratolytic agents, desquamating agents, keratinocyte proliferation enhancers, and skin plumpers that serve as additional collagen enhancers to the skin, to name a few. An example of a suitable skin plumper is palmitoyl oligopeptide. Other skin plumping agents include other collagen and/or other glycosaminoglycan (GAG) enhancing agents. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof. In some embodiments, the invention relates to synergistic action of one or more compositions described herein with TDPA, e.g., to provide enhanced anti-aging benefits to skin. Additional examples of anti-aging agents are provided below.

The compositions described herein can be formulated as a variety of skin care products for topical application. The composition may be formulated in a variety of product forms suitable for application to the skin (including the scalp and/or hair), such as, for example, a lotion, cream, serum, spray, aerosol, cake, ointment, essence, gel, paste, patch, pad, pencil, pomade, solution, towelette, mask, stick, foam, elixir, mousse, powder, bath salt, foaming cleanser, concentrate, or any other liquid, semi-solid, or solid form. Preferably the composition is formulated as a lotion, cream, essence, ointment, or gel, and in particular a lotion, toner pad or cleanser, e.g., for anti-acne products.

For example, the potassium, zinc, calcium, rubidium or a combination thereof may be present in an amount from about 0.001 weight % to about 5 weight % based on the total weight of the composition; from about 0.01 weight % to about 3 weight % based on the total weight of the composition; and from about 0.1 weight % to about 2 weight %, or about 1 weight %, based on the total weight of the composition.

The compositions can include a cosmetically acceptable vehicle. A cosmetically acceptable vehicle refers to any vehicle, for a cosmetic, drug or medicament that is suitable for use in direct, safe contact with human tissues and/or human hair, and may include, e.g., any diluent, solvent, carrier, filler, or the like. Such vehicles may take the form of any known in the art suitable for application to skin (or hair) and may include water (e.g., deionized water); vegetable oils; mineral oils; esters such as octal palmitate, isopropyl myristate, and isopropyl palmitate; ethers such as dicapryl ether and dimethyl isosorbide; alcohols such as ethanol and isopropanol; fatty alcohols such as cetyl alcohol, cetearyl alcohol, stearyl alcohol, and biphenyl alcohol; isoparaffins such as isooctane, isododecane, and isohexadecane; silicone oils such as cyclomethicone, dimethicone, dimethicone cross-polymer, polysiloxanes, and their derivatives, preferably organo-modified derivatives; hydrocarbon oils such as mineral oil, petrolatum, isoeicosane, and polyisobutene; polyols such as propylene glycol, glycerin, butylene glycol, pentylene glycol, and hexylene glycol; waxes such as beeswax and botanical waxes; or any combinations or mixtures of the foregoing. Based on the teachings herein, a person skilled in the art will be able to select a suitable vehicle, and/or in an amount thereof, such that one or more of the desired properties of the cosmetic compositions of the instant invention can be preserved. The vehicle may comprise an aqueous phase, an oil phase, an alcohol phase, a silicone phase, or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions, or the like having the appearance of a cream, gel, or microemulsions. The emulsion may include an emulsifier, such as a nonionic, anionic or amphoteric surfactant. The oil phase of the emulsion preferably has one or more organic compounds, including emollients; humectants, such as butylene glycol, propylene glycol, Methyl gluceth-20, and glycerin; other water-dispersible or water-soluble components, including thickeners such as veegum or hydroxyalkyl cellulose; gelling agents, such as high MW polyacrylic acid and mixtures thereof. The emulsion may have one or more emulsifiers capable of emulsifying the various components present in the composition. The compounds suitable for use in the oil phase include without limitation, vegetable oils; esters such as octyl palmitate, isopropyl myristate, and isopropyl palmitate; ethers such as dicapryl ether; fatty alcohols such as cetyl alcohol, stearyl alcohol, and behenyl alcohol; isoparaffins such as isooctane, isododecane, and isohexadecane; silicone oils such as dimethicones, cyclic silicones, and polysiloxanes; hydrocarbon oils such as mineral oil, petrolatum, isoeicosane, and polyisobutene; natural or synthetic waxes; and the like. The oil-containing phase may be composed of a single oil or mixtures of different oils. Suitable hydrophobic hydrocarbon oils may be saturated or unsaturated, have an aliphatic character, be straight or branched chained, or contain alicyclic or aromatic rings. Hydrocarbon oils include those having 6-20 carbon atoms, more preferably 10-16 carbon atoms. Representative hydrocarbons include decane, dodecane, tetradecane, tridecane, and C8-20 isoparaffins. Paraffinic hydrocarbons are available from Exxon under the ISOPARS trademark, and from the Permethyl Corporation. In addition, C8-20 paraffinic hydrocarbons such as C12 isoparaffin (isododecane) manufactured by the Permethyl Corporation having the trade name Permethyl 99 ATM are also contemplated to be suitable. Various commercially available C16 isoparaffins, such as isohexadecane are also suitable. Examples of preferred volatile hydrocarbons include polydecanes, such as isododecane and isodecane, including for example, Permethyl-99A and the C7-C8 through C12-C15 isoparaffins.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof. Non-limiting emulsifiers include emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. Some preferred emulsifiers include soya sterol, cetyl alcohol, stearic acid, emulsifying wax, acrylates, silicone containing emulsifiers, and mixtures thereof. Other specific emulsifiers that can be used with the compositions described herein include, but are not limited to, one or more of the following: C.sub.10-30 alkyl acrylate cross polymer; Dimethicone PEG-7 isostearate; acrylamide copolymer; mineral oil; sorbitan esters; polyglyceryl-3-diisostearate; sorbitan monostearate; sorbitan tristearate; sorbitan sesquioleate; sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference. These emulsifiers typically will be present in the composition in an amount from about 0.001% to about 10% by weight, in particular in an amount from about 0.01% to about 5% by weight, and more preferably, from about 0.1% to about 3% by weight. Based on the teachings herein, a person skilled in the art will be able to select a suitable emulsifier, or any other materials described herein, and/or in an amount thereof, such that one or more of the desired properties of the cosmetic compositions of the instant invention can be preserved.

The oil phase may comprise one or more volatile and/or non-volatile silicone oils. Volatile silicones include cyclic and linear volatile dimethylsiloxane silicones. In some embodiments, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few. The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like. The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration. Additional suitable delivery vehicles include, e.g., niosomes, submicron emulsions, polymeric encapsulants, gels, creams, lotions, and combinations thereof.

The composition may optionally comprise other cosmetic actives and excipients, obvious to those skilled in the art including, but not limited to, fillers, emulsifying agents, surfactants, film formers, chelating agents, such as EDTA, gelling agents, thickeners, emollients, humectants, moisturizers, vitamins, minerals, viscosity and/or rheology modifiers, sunscreens, retinoids, hormonal compounds, alpha-hydroxy acids, alpha-keto acids, anti-mycobacterial agents, antifungal agents, antimicrobials, antivirals, analgesics, lipidic compounds, antineoplastics, immune system boosting agents, anti-allergenic agents, H1 or H2 antihistamines, anesthetics, antiseptics, insect repellents, skin cooling compounds, skin protectants, skin penetration enhancers, exfollients, lubricants, fragrances, colorants, hypopigmenting agents, preservatives, stabilizers, pharmaceutical agents, photostabilizing agents, neutralizers, and mixtures thereof. In addition to the foregoing, the cosmetic compositions of the invention may contain any other compound for the treatment of skin conditions or disorders. Based on the teachings herein, a person skilled in the art will be able to select any of these or other materials, and/or in an amount thereof, such that one or more of the desired properties of the cosmetic compositions of the instant invention can be preserved. Preservatives may include, for example, alcohols, glycols, parabens, quaternary nitrogen-containing compounds, isothiazolinones, aldehyde-releasing agents, antioxidants, halogenated compounds, and combinations thereof. Illustrative alcohols include, e.g., phenoxyethanol, isopropyl alcohol, and benzyl alcohol; illustrative glycols include, e.g., propylene, butylene, and pentylene glycol; illustrative parabens include, e.g., methyl, propyl and butyl-parabens; illustrative quaternary nitrogen-containing compounds include, e.g., benzalkonium chloride and Quaternium 15; illustrative isothiazolinones include, e.g., methylisothiazolinone and methylchloroisothiazolinone; illustrative aldehyde-releasing agents include, e.g., DMDM hydantoin, imidazolidinyl urea, and diazolidinyl urea; illustrative antioxidants include, e.g., butylated hydroxytoluen and tocopherol, and illustrative halogenated compounds include, e.g., triclosan and chlorohexidine digluconate.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders, polyethylene powder, starch, boron nitride, copolymer microspheres, and silicone resin microbeads and the like.

The number of applications of a composition to the skin that will generally be effective for producing one or more desired effects, as are described herein, and the period of time during which such applications are made, may vary widely, depending upon a variety of factors, such as the concentration of the one or more active agents that are present in the composition, the amount of the composition that is applied to the skin, the condition of the skin, the amount of the sun exposure and the type, age, sex, genetic predisposition and general health of the mammal, and may readily be determined by those having ordinary skill in the art using the information provided herein. While the skin may exhibit some improvement after only one application of a composition thereto, in order to obtain a more pronounced or full effect or benefit, it is typically beneficial to provide two or more applications to the skin, and more typically beneficial to provide at least about three applications of the composition to the skin (three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth applications) continuously over a period of at least about one day or week, or a series of days or weeks (one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth days or one, two, three, four, five, six, seven, eight, nine, ten, eleven, twelve, and so forth weeks). The compositions may, for example, be applied as a solid stick (or other solid form), a cream, a gel, a lotion, an ointment or other convenient form as frequently as once per 15 minutes (or per fewer minutes, such as 1, 5 or 10 minutes) and as infrequently as once per day or so or on an "as needed" basis (i.e., applied as believed to be necessary or desirable, or required, typically depending upon the types and severity of symptoms). Thus, as only by way of some examples, the following quantities of compositions within the present invention, or others, may be administered to a user per application (in g or ml), as well as any quantities in between: 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9. 7.0, 7.1, 7.2, 7.3, 7.4, 7.5, 7.6, 7.7, 7.8, 7.9, 8.0. 8.1, 8.2, 8.3, 8.4, 8.5, 8.6, 8.7, 8.8, 8.9, 9.0. 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, 20.1, 20.2, 20.3, 20.4, 20.5, 20.6, 20.7, 20.8, 20.9, 21, 22, 23, 24, 25, 26, 27, 28, 29, 30, 31, 32, 33, 34, 35, 36, 37, 38, 39, 40 and so forth.

In one aspect, the present invention provides a composition for topical application to the skin for repairing, improving or fully healing a skin disorder, disease or condition, or for causing the skin to experience a reduction in pain, soreness or itchiness, or an increase in soothing, softening or conditioning, or a combination thereof, comprising: (a) one or a plurality of active agents, such as hydrocortisone, wherein the active agents are present in the composition in a combined amount that is effective for repairing, improving or healing the skin, or causing the skin to experience a reduction in pain, soreness or itchiness, or an increase in soothing, softening or conditioning, or a combination thereof, after a topical application of the composition to the skin; and (b) a base composition, wherein the base composition is present in the composition in an amount that is effective for permitting the base composition to function effectively as a carrier vehicle for the active agents when topically applied to the mammal's skin.

In still another aspect, the present invention provides a method for repairing, improving or fully healing a skin disorder, disease or condition of a mammal, or for causing the skin to experience a reduction in pain, soreness or itchiness, or an increase in soothing, softening or conditioning, or a combination thereof, comprising topically applying to the mammal's skin on a regular basis at least one or two applications of one of the above compositions, wherein the amount of the composition that is applied to the skin is effective for repairing, improving or fully healing a skin disorder, disease or condition of the mammal, or for causing the mammal's skin to experience a reduction in pain, soreness or itchiness, or an increase in soothing, softening or conditioning, or a combination thereof, and wherein the temperature of the composition is optionally elevated to a temperature above ambient temperature prior to topically applying the composition to the mammal's skin.

In still another aspect, the present invention provides a method for repairing, improving or fully healing a skin disorder, disease or condition of a mammal, or for causing the mammal's skin to experience a reduction in pain, soreness or itchiness, or an increase in soothing, softening or conditioning, or a combination thereof, consisting of (or consisting essentially of) topically applying to the mammal's skin on a regular basis at least one or two applications of one of the above compositions, wherein the amount of the composition that is applied to the skin of the mammal is an amount that is effective for repairing, improving or fully healing a skin disorder, disease or condition of the mammal, or for causing the mammal's skin to experience a reduction in pain, soreness or itchiness, or an increase in soothing, softening or conditioning, or a combination thereof.

In a preferred embodiment, the skin condition to be treated is one or more of the conditions that may be referred to collectively as the signs of skin aging. The appearance of skin normally changes with age, due to a number of internal factors associated with time. However, the skin can also be prematurely aged by virtue of its overexposure to environmental factors such as sun, pollution, or cigarette smoke. As used herein, the regulation of skin conditions resulting from aging is intended to encompass both the signs of chronoaging as well as photo- or environmentally-induced aging. The manifestations of the aging process are many, and may be both external (i.e., immediately visible) or internal (i.e., not immediately visible to the naked eye). Those skilled in the art will readily recognize the numerous examples of the signs of aging. Such examples include, without limitation, fine lines and wrinkles, deep wrinkles, pitting and bumps, increased pore size, keratosis, skin flakiness or roughness, unevenness or blotching of skin tone, yellowing of the skin, dark under eye shadows or circles, loss of skin elasticity, sagging (including puffiness in the eye area and jowls), elastosis, loss of skin firmness or tightness, hyperpigmentation, age spots and freckles, abnormal differentiation, hyperkeratinization, collagen breakdown, spider veins, or telangiectasia, among others.

The composition can further contain a surface-active agent. Surface-active agents (also termed "surfactants") include any agent linking oil and water in the composition, in the form of emulsion. The composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, brij 38, brij 52, brij 56 and brij W1, a sucrose ester, a partial ester of sorbitol and its anhydrides, sorbitan monolaurate, sorbitan monolaurate a monoglyceride, a diglyceride, isoceteth-20 and mono-, di- and tri-esters of sucrose with fatty acids.

In an embodiment, the additional component is a humectant, a substance that helps retain moisture and also prevents rapid evaporation. Suitable humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof. Pharmaceutical compositions may in one or more embodiments comprise a moisturizer or combinations thereof.

In an embodiment, a composition includes one or more additional components. Such additional components include but are not limited to buffering agents, bulking agents, chelating agents, cleansers, colorants, conditioners, diluents, dyes, emollients, fragrances, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, and viscosity modifiers. As is known to one skilled in the art, in some instances a specific additional component may have more than one activity, function or effect. In an embodiment, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof. In an embodiment, the additional component is an emollient. Suitable emollients include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9-15 alcohols, isononyl iso-nonanoate, silicone oils, polyethers, C12-15 alkyl benzoates, oleic acid, stearic fatty acid, cetyl alcohols, hexadecyl alcohol, dimethyl polysiloxane, polyoxypropylene cetyl ether, polyoxypropylene butyl ether, and derivatives, esters, salts and mixtures thereof. In an embodiment, the additional component is a preservative. Suitable preservatives include but are not limited to alkyl benzoates, alkyl p-hydroxybenzoates, aloe vera extract, ascorbic acid, benzalkonium chloride, benzoic acid, benzoic acid esters of C9-15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyethers, polyoxypropylene butyl ether, polyoxypropylene cetyl ether, potassium sorbate, silicone oils, sodium propionate, sodium benzoate, sodium bisulfate, sorbic acid, stearic fatty acid, vitamin E, vitamin E acetate and derivatives, esters, salts and mixtures thereof.

In an embodiment, the additional component is a skin penetration enhancer. Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl)ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethyl-hexyl pelargonate, ethyl-2-hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly(dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly (dimethylaminoethylmethacryl-ate), quaternised poly (vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolamine oleate, urea, water and derivatives, esters, salts and mixtures thereof.

Lubricants may be introduced into any of the formulations to reduce friction during application. This may be useful for producing a good skin feeling or ease of body cavity use. Any pharmaceutically or cosmetically acceptable lubricant may be used. Non limiting examples of general categories of lubricants are; polymeric substances such as celluloses, natrosol; hyaluronic acid; glycerin; silicones (e.g. dimethicone); and oil based lubricants such as plant based oils (e.g. olive oil, sweet almond oil; avocado oil and the like); petrolatum; and fats. In some situations it may be appropriate to select a polymeric agent having a viscosity and also a lubricating effect such that it has some adherence to the site of application but displays a reduced friction and is easier and more pleasant to use.

In addition the present invention may include an elemental metal, selected from the group consisting of silver, copper, zinc, mercury, tin, lead, bismutin, cadmium, chromium and/or gold.

The topical carrier in liquid hair or skin compositions may be water, common organic solvents, or mixtures thereof. Suitable common organic solvents are C2-C3 lower monohydric or polyhydric alcohols such as ethanol, propanol, isopropanol, glycerin, dimethylformamide, dimethylacetamide, and dimethylsulfoxide. In addition the present invention may include one or more selected from detersive surfactants, anionic surfactants, nonionic surfactants, amphoteric surfactants, zwitterionic surfactants, cationic surfactants, volatile carriers, azoles, selenium sulfides, sulfur, suspending agents, thickening agents, polymers, spreading agents, hydrocarbon oils, polyolefin, fatty esters, polyalkylene glycols.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A topical composition for application to a keratinous tissue comprising:
 a cosmetically or pharmaceutically acceptable carrier;
 a concentration of from about 0.001 weight % to about 5 weight % individually of potassium, zinc, calcium, and rubidium; or
 an individual concentration of from about 0.001 weight % to about 5 weight % individually of potassium, zinc and rubidium
 disposed in the cosmetically or pharmaceutically acceptable carrier; and
 one or more peptides disposed in the cosmetically or pharmaceutically acceptable carrier, wherein the one or more peptides comprise a dipeptide, a tetrapeptide, a hexapeptide, a tripeptide, a pentapeptide, a heptapeptide, an octapeptide, an enneapeptide or a decapeptide.

2. The composition of claim 1, wherein the composition comprises potassium, zinc, calcium, and rubidium.

3. The composition of claim 1, wherein the composition comprises potassium, zinc and rubidium.

4. The composition of claim 1, comprising potassium, zinc, calcium, and rubidium in an individual concentration of from about 0.01 weight % to about 3 weight % individual for potassium, zinc, calcium, and rubidium based on the total weight of the composition;

from about 0.1 weight % to about 2 weight % individual for potassium, zinc, calcium, and rubidium based on the total weight of the composition, or about 1 weight %, individual for potassium, zinc, calcium, and rubidium based on the total weight of the composition.

5. The composition of claim 1, comprising 0.01-5% potassium, 0.01-5% zinc, 0.01-1% calcium, and 0.01-1% rubidium.

6. The composition of claim 1, wherein the one or more peptides are fragments of protein molecules that naturally occur in the skin.

7. The composition of claim 1, wherein the one or more peptides comprise a dipeptide-2, a tetrapeptide-3, or a acetyl hexapeptide-3.

8. The composition of claim 1, wherein the one or more peptides comprise acetyl hexapeptide-3.

9. The composition of claim 8, wherein the one or more peptides comprise 0.05 to 5% acetyl hexapeptide-3.

10. The composition of claim 1, wherein the topical composition is in the form of a lotion, cream, essence ointment, gel, emulsion, pack, cosmetic liquid, ointment, pharmaceutical or stick.

11. The composition of claim 1, further comprising oak bark extract, soy extract, retinoid, or glycerin.

12. The composition of claim 1, further comprising a phytoestrogen in a topical composition in the form of an eye cream, a sesame protein in a topical composition in the form of a day cream or a walnut extract in a topical composition in the form of a night cream.

13. The composition of claim 1 further comprising at least one skin benefit agent selected from the group consisting of astringents, antioxidants, free radical scavengers, anti-acne agents, antimicrobial agents, antifungal agents, chelating agents, anti-aging agents, anti-wrinkle agents, analgesics, skin lightening agents, skin conditioning agents, anti-irritants, anti-inflammatories, anti-cellulite agents, humectants, emollients, organic sunscreens, inorganic sun protecting agents, chemical exfoliating agents, physical exfoliating agent, self-tanning agents, biologically active peptides and mixtures thereof.

* * * * *